(12) United States Patent
Martins et al.

(10) Patent No.: US 8,492,341 B2
(45) Date of Patent: Jul. 23, 2013

(54) AMYLOID-β BINDING PEPTIDES

(75) Inventors: Ralph Martins, Maddington (AU); Trevor Payne, Ballingup (AU)

(73) Assignee: Alzyme Pty Ltd., Perth (AU)

( * ) Notice: Subject to any disclaimer, the term of this patent is extended or adjusted under 35 U.S.C. 154(b) by 138 days.

(21) Appl. No.: 12/514,738

(22) PCT Filed: Nov. 15, 2007

(86) PCT No.: PCT/AU2007/001767
§ 371 (c)(1), (2), (4) Date: Mar. 16, 2010

(87) PCT Pub. No.: WO2008/064401
PCT Pub. Date: Jun. 5, 2008

(65) Prior Publication Data
US 2010/0173850 A1 Jul. 8, 2010

(30) Foreign Application Priority Data
Nov. 28, 2006 (AU) .............................. 2006906668

(51) Int. Cl.
*A61K 38/08* (2006.01)
*A61P 25/28* (2006.01)
*C07K 7/06* (2006.01)
*C07K 1/06* (2006.01)
*A61K 51/12* (2006.01)

(52) U.S. Cl.
USPC ......... 514/17.7; 514/17.8; 530/328; 530/329; 530/330; 530/335; 424/1.69

(58) Field of Classification Search
None
See application file for complete search history.

(56) References Cited

U.S. PATENT DOCUMENTS

| 4,179,337 A | 12/1979 | Davis et al. | |
| 6,245,886 B1 * | 6/2001 | Halazonetis et al. | 530/332 |
| 2004/0192901 A1 * | 9/2004 | Martins | 530/400 |
| 2007/0093415 A1 * | 4/2007 | Martin | 514/12 |

FOREIGN PATENT DOCUMENTS

| WO | 03/056339 | 7/2003 |
| WO | 03/076455 | 9/2003 |
| WO | 2006/031330 | 3/2006 |

OTHER PUBLICATIONS

Honigman et al., Mol. Ther., 4:239-249 (2001).
International Search Report in PCT/AU07/01767, dated Dec. 7, 2007.
Mehta et al., Arch. Neurol., 57(1):100-105 (2000).
Permanne et al., FASEB J., 16:860-862 (2002).
Yang et al., Proc. Natl. Acad. Sci. USA, 98:2616-2621 (2001).
Abuchowski et al., Enzymes as drugs, 367-383 (1981).
Berridge et al., Arch. Biochem. Biophys., 303:474-482 (1993).
Atwood et al., Cell Mol. Biol., 46:777-783 (2000).
Atwood et al., Biochemistry, 43:560-568 (2004).
Fahey, Radiol. Clin. North Am., 39:919-929 (2001).
Goldsmith et al., Radiol. Clin. North Am., 38:511-524 (2000).
Petanceska et al., Neurology, 54(12):2212-2217 (2000).

* cited by examiner

*Primary Examiner* — Elizabeth C Kemmerer
*Assistant Examiner* — Kimberly A Ballard
(74) *Attorney, Agent, or Firm* — McAndrews, Held & Malloy, Ltd.

(57) ABSTRACT

A peptide sequence of the form: X(Lys,Arg)XXXXX(Arg,Lys)X, wherein Lys and Arg are replaceable and X is preferably one or more of the following amino acids: hydrophobic amino acid residues (eg Pro, Leu, Met, Ile), basic amino acid residues or threonine; and wherein the sequence is capable of engaging Aβ and ameliorating its SOD activity and/or metal ion binding.

7 Claims, 8 Drawing Sheets

SEQUENCE LISTING

<160> NUMBER OF SEQ ID NOS: 9

<210> SEQ ID NO 1
<211> LENGTH: 4
<212> TYPE: PRT
<213> ORGANISM: Artificial Sequence
<220> FEATURE:
<223> OTHER INFORMATION: Synthetic

<400> SEQUENCE: 1

Pro Gln Met Leu
1

<210> SEQ ID NO 2
<211> LENGTH: 9
<212> TYPE: PRT
<213> ORGANISM: Artificial Sequence
<220> FEATURE:
<223> OTHER INFORMATION: Synthetic

<400> SEQUENCE: 2

Asn Arg Thr Pro Gln Met Leu Lys Arg
1               5

<210> SEQ ID NO 3
<211> LENGTH: 15
<212> TYPE: PRT
<213> ORGANISM: Artificial Sequence
<220> FEATURE:
<223> OTHER INFORMATION: Synthetic

<400> SEQUENCE: 3

Thr Asn Pro Asn Arg Arg Asn Arg Thr Pro Gln Met Leu Lys Arg
1               5                   10                  15

<210> SEQ ID NO 4
<211> LENGTH: 7
<212> TYPE: PRT
<213> ORGANISM: Artificial Sequence
<220> FEATURE:
<223> OTHER INFORMATION: Synthetic

<400> SEQUENCE: 4

Arg Thr Pro Gln Met Leu Lys
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic

<400> SEQUENCE: 5

Thr Arg Thr Pro Gln Met Leu Arg Lys
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(9)
<223> OTHER INFORMATION: D-isomer of amino acid

```
<400> SEQUENCE: 6

Arg Lys Leu Met Gln Pro Thr Arg Asn
1               5

<210> SEQ ID NO 7
<211> LENGTH: 4
<212> TYPE: PRT
<213> ORGANISM: Artificial Sequence
<220> FEATURE:
<223> OTHER INFORMATION: Synthetic

<400> SEQUENCE: 7

Gly Gly Gly Gly
1

<210> SEQ ID NO 8
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (2)..(2)
<223> OTHER INFORMATION: is Lys or Arg
<220> FEATURE:
<221> NAME/KEY: misc_feature
<222> LOCATION: (3)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: is Lys or Arg
<220> FEATURE:
<221> NAME/KEY: misc_feature
<222> LOCATION: (9)..(9)
<223> OTHER INFORMATION: Xaa can be any naturally occurring amino acid

<400> SEQUENCE: 8

Xaa Xaa Xaa Xaa Xaa Xaa Xaa Xaa Xaa
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: is Lys or Arg
<220> FEATURE:
<221> NAME/KEY: misc_feature
<222> LOCATION: (2)..(6)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: is Lys or Arg

<400> SEQUENCE: 9

Xaa Xaa Xaa Xaa Xaa Xaa Xaa
1               5
```

AMYLOID-β BINDING PEPTIDES

The present application is filed pursuant to 35 U.S.C. 371 as a U.S. National Phase application of International Patent Application No. PCT/AU07/01767, which was filed Nov. 15, 2007, claiming the benefit of priority to Australian Patent Application No. 2006906668, which was filed on Nov. 28, 2006. The entire text of the aforementioned applications is incorporated herein by reference in its entirety.

FIELD OF THE INVENTION

The present invention relates to agents and methods for treating diseases such as Alzheimer's disease and other diseases with similar causative agents and to methods for identifying agents for use in treating Alzheimer's disease and other diseases with similar causative agents. More particularly, the present invention relates to novel peptides and their use to treat Alzheimer's disease and methods for screening of peptides to identify peptides for use in treating Alzheimer's disease.

BACKGROUND

Alzheimer's disease (AD) is a progressive neurodegenerative disorder characterised pathologically by the deposition of amyloid plaques and neurofibrillary tangles, and neuronal degeneration, in the brains of affected individuals.

The major protein component of the amyloid deposits is a small 4 kDa peptide of 39-43 amino acids termed beta amyloid (β-amyloid or Aβ). Aβ, is a small protein thought to be central to the pathogenesis of AD. Numerous studies have suggested that Aβ accumulation and deposition may be critical to AD. The initial deposition of Aβ and growth of plaques has been suggested to occur via distinct processes. Aβ may either form higher oligomeric structures or remain in the monomeric form when it is deposited. In vitro studies have found that freshly solubilsed monomeric Aβ, at low concentrations, is not toxic to neurons in culture. However, after an aging period of several hours to days Aβ spontaneously aggregates in solution to form fibrillar entities that are highly neurotoxic. This suggests aggregation is a requirement for Aβ toxicity.

The AD brain has been shown to be under oxidative stress. Oxidative stress is a situation where there is an excess of oxygen free radicals or reactive oxygen species (ROS), which in turn damage surrounding tissue. Important ROS that damage the surrounding cellular components are the superoxide radical, hydrogen peroxide and the hydroxyl radical.

Superoxide dismutases (SOD) are metalloenzymes containing a redox-active transition metal (copper, iron or manganese) at the active site. SOD enzymes (SODs) dismutate superoxide radicals by electron transfer between superoxide anions and the transition active metal. While low levels of SODs do provide some protection by detoxifying superoxide radicals thereby preventing superoxide mediated cell damage, high levels of these enzymes sensitises cells to oxidative stress by the overproduction of hydrogen peroxide.

There is overwhelming evidence that supports the notion that the toxicity associated with human Aβ is largely dependent on its superoxide dismutase (SOD)-like activity and that this activity is copper dependent. These findings have led to the development of copper chelating agents for treating AD. However, whilst copper chelators may inhibit the SOD activity of Aβ, they are non-specific and the chelation of copper may disrupt essential biochemical functions in the brain and result in undesirable side effects.

Other diseases such as type II diabetes, Scrapie and Transmissible Spongiform Encephalopathies such as Creutzfeldt Jacob disease (CJD), variant CJD, Gerstmann Strausler Schinkler syndrome, Inclusion-Body Myositis and Bovine Spongiform Encephalopathy (BSE) have also been linked with SOD activity.

In PCT/AU02/01754 there is described a novel screening method involving phage display technology to identify novel peptides capable of inhibiting Aβ's neurotoxicity. Various phage libraries, each containing millions of peptides, were screened with random 6- or 15-amino acid sequences. After various rounds of panning, three sequences were selected.

The three candidate peptides (15merTNP, 6merPLP and 6merMTM) were examined to determine whether they could attenuate Aβ's SOD-like activity in vitro. A DCF fluorescence assay was used to assess the efficacy of these peptides on altering the production of physiological (brain) concentrations (200 nM) of human Aβ1-42. Results from these studies revealed that all three possessed the ability to modify Aβ1-42's SOD-like activity.

While the aforementioned research identified various candidate peptides that displayed an activity that attenuated Aβ's SOD-like activity in vitro, delivery of peptides to patients requires a biological agent that is a conformational match to the active site on the Aβ therein permitting attenuation of Aβ's SOD-like activity. Further, the amino acid sequence should preferably be as short as possible and confined in a structural manner that permits biological interaction while preserving maximum stability and longevity of the sequence in vivo.

The present invention seeks to provide an agent that ameliorates SOD activity and/or metal ion binding of causative agents such as Aβ. The invention further seeks to present efficacious treatment options for treatment of AD and other SOD related diseases.

General

Those skilled in the art will appreciate that the invention described herein is susceptible to variations and modifications other than those specifically described. The invention includes all such variation and modifications. The invention also includes all of the steps, features, formulations and compounds referred to or indicated in the specification, individually or collectively and any and all combinations or any two or more of the steps or features.

Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness. None of the cited material or the information contained in that material should, however be understood to be common general knowledge.

Manufacturer's instructions, descriptions, product specifications, and product sheets for any products mentioned herein or in any document incorporated by reference herein, are hereby incorporated herein by reference, and may be employed in the practice of the invention.

The present invention is not to be limited in scope by any of the specific embodiments described herein. These embodiments are intended for the purpose of exemplification only. Functionally equivalent products, formulations and methods are clearly within the scope of the invention as described herein.

The invention described herein may include one or more range of values (eg size, concentration etc). A range of values will be understood to include all values within the range, including the values defining the range, and values adjacent to the range which lead to the same or substantially the same outcome as the values immediately adjacent to that value which defines the boundary to the range.

Throughout this specification, unless the context requires otherwise, the word "comprise" or variations such as "comprises" or "comprising", will be understood to imply the inclusion of a stated integer or group of integers but not the exclusion of any other integer or group of integers.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

SUMMARY OF THE INVENTION

1. The present invention provides a peptide sequence of the form:

$$X(Lys, Arg)XXXXX(Arg, Lys)X, \quad (SEQ\ ID\ NO:\ 8)$$

wherein Lys and Arg are replaceable and X is preferably one or more of the following amino acids: hydrophobic amino acid residues (eg Pro, Leu. Met, Ile), basic amino acid residues or threonine; and wherein the sequence is capable of engaging Aβ and ameliorating its SOD activity and/or metal ion binding.

According to another aspect, the present invention provides a method for altering abnormal SOD activity and/or abnormal metal ion binding activity, said method comprising the step of: contacting a peptide as described herein with an agent that causes the abnormal SOD activity and/or abnormal metal ion binding, under conditions that promote contact of the peptide with the agent and causes the SOD activity and/or metal ion binding to alter.

The invention also provides a method for reducing the SOD activity or inhibiting the copper binding ability of Aβ in a patient, the method comprising the step of: contacting Aβ with a peptide as described herein such that the peptide binds to Aβ in a fashion that at least reduces its SOD and/or copper binding activity.

The invention also relates to a method for destabilizing multimeric forms of Aβ, comprising the step of: contacting a peptide sequence of the present invention with Aβ under conditions that facilitate binding of the peptide to the Aβ protein.

A method for ameliorating or preventing the aggregation of Aβ in a patient, comprising the step of: contacting a therapeutically effective amount of a peptide of the present invention with Aβ under conditions that facilitate binding of the peptide to the Aβ protein.

In yet another aspect, the present invention provides a method for ameliorating or preventing a disease or disorder associated with abnormal SOD activity and/or abnormal metal ion binding, comprising the step of: administering a pharmaceutical composition or medicament comprising a peptide as described herein to a patient susceptible to, or otherwise at risk of, a disease or disorder associated with abnormal SOD activity and/or metal ion binding in an amount sufficient to eliminate or reduce the risk or delay the outset of the disease.

Further, the invention relates to methods for ameliorating or preventing the aggregation of Aβ in a patient, comprising the step of: contacting a therapeutically effective amount of peptide sequence of the present invention with Aβ under conditions that facilitate binding of the peptide to the Aβ protein.

The present invention also concerns a method for treating or preventing an amyloid disease or disorder comprising the step of: administering to the patient an effective amount of a peptide as described herein under conditions which promote contact of the peptide with the causative agent of the disease or disorder.

The present invention also concerns a method for treating or preventing a disease or disorder selected from the group comprising: type II diabetes, AD, Scrapie and Transmissible Spongiform Encephalopathies such as Creutzfeldt Jacob disease (CJD), variant CJD, Gerstmann Strausler Schinkler syndrome, Inclusion-Body Myositis and Bovine Spongiform Encephalopathy (BSE) comprising the step of: administering to the patient an effective amount of a peptide as described herein.

In one particular aspect, the invention provides an AD monitoring system, which comprises: a peptide of the invention and a label useful for imaging by PET or SPECT or MRI or fluorescent imaging modalities.

In another aspect the invention provides an in vivo detection method of AD in a patient, which method comprises the steps of: administering a labelled peptide according to the present invention to the patient and detecting the presence of the labelled peptide bound to the tissue in the patient by a known imaging technique. Imagining techniques that will have particular use with the present invention include PET, SPECT or MRI or fluorescent imaging modalities.

Other aspects and advantages of the invention will become apparent to those skilled in the art from a review of the ensuing description, which proceeds with reference to the following illustrative drawings.

DETAILED DESCRIPTION OF THE INVENTION

Figure 1:
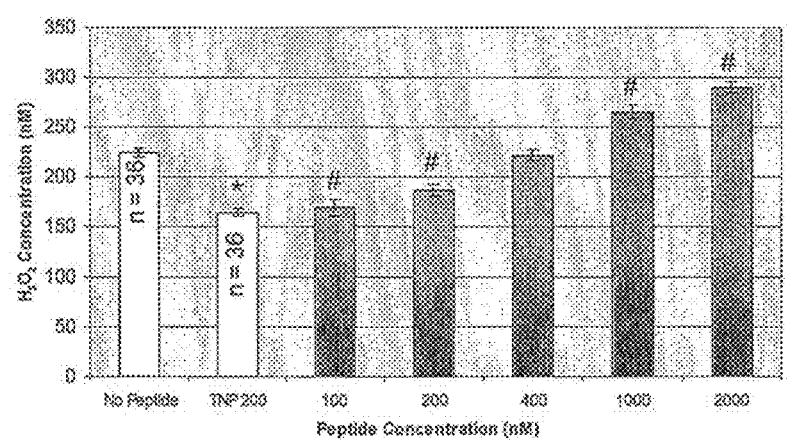
FIG. 1 illustrates the effect of SEQ ID NO: 2 on $H_2O_2$ production by 200 nM Human Aβ1-42. SEQ ID NO: 2: ANOVA; $F_{(6,110)}=64.31$, $P<0.001$; Post-Hoc (Bonferroni) #$P<0.001$ vs human Aβ1-42 (no peptide).

According to the invention, the inventors have revealed that peptides that are rich in proline, methionine, arginine and other basic residues (eg His and Lys) with a core structure of (Lys,Arg)XXXXX(Lys,Arg) (SEQ ID NO:9) engage Aβ, wherein Lys and Arg are replaceable and X is preferably an amino acid selected from one or more of the following: hydrophobic amino acid residues (eg Pro, Leu. Met, Ile), basic amino acid residues or threonine.

The present invention therefore provides a peptide sequence of the form (SEQ ID NO: 8)
X(Lys, Arg)XXXXX(Arg, Lys)X, where Lys and Arg are replaceable and X is preferably an amino acid selected from one or more of the following: hydrophobic amino acid residues (eg Pro, Leu, Met, Ile), basic amino acid residues or threonine; and wherein the sequence is capable of engaging Aβ and ameliorating its SOD activity and/or metal ion binding. Preferably, the sequence is provided in a pharmaceutically acceptable form.

Preferably, the XXXXX region in the core sequence will include the sequence Pro-Gln-Met-Leu (SEQ ID NO:1). More preferably, the sequence will be devoid of one or more acidic amino acid residues (eg Glu and Asp), hydrophobic aromatic residues (eg Phe, Tyr, Trp), alanine, glycine, valine or cysteine. By way of example the peptide sequence is:

(SEQ ID NO: 2)
H-Asn-Arg-Thr-Pro-Gln-Met-Leu-Lys-Arg-OH

In a variant aspect of the invention, the core structure is truncated at the (Lys,Arg) at the amino or carboxyl end. In a further variant form of the invention the herein described sequence may be truncated at both its amino and carboxyl ends. Any truncation of the sequence should not substantially alter the sequence's capacity to engage Aβ. Any truncation of the peptide sequence can result in 1, 2, 3, 4 amino acids being deleted but will not effect the binding ability of the sequence.

The therapeutic effectiveness of the above peptides are determined by many factors, one of which is the in vivo stability of the sequence. According to the invention the inventors have revealed that end protection of the peptides of the invention can substantially increase the half life of the peptide sequence. Accordingly, the peptide sequence employed herein is preferably modified in a manner which substantially protects the amino end and/or carboxyl end of the sequence.

The peptides encompassed within the scope of the present invention are capable of disrupting SOD activity by interfering with copper binding. Such peptides may bind directly to a copper binding site associated with a causative agent for an amyloid disease or disorder or like disease and thus directly block or otherwise interfere with copper binding. Alternatively, they may bind at a site other than the copper binding site and indirectly block copper binding by causing some conformational change that removes or otherwise affects the copper binding site to the extent that its ability to bind copper is at least diminished and preferably totally removed. It is also envisaged that peptides isolated using the screening method may disrupt SOD activity without necessarily preventing copper binding.

The causative agent may be a prion protein, Aβ or amylin. Furthermore, the disease or disorder may be selected from the group comprising: type II diabetes, AD, Scrapie and Transmissible Spongiform Encephalopathies such as Creutzfeldt Jacob disease (CJD), variant CJD, Gerstmann Strausler Schinkler syndrome, Inclusion-Body Myositis and Bovine Spongiform Encephalopathy (BSE). Preferably, the disease or disorder is AD.

Preferably, the peptides of the present invention totally remove SOD activity and/or prevent the causative agent binding copper. However, it will be appreciated that peptides that decrease the SOD activity and/or copper binding activity are also useful. The peptides of the present invention may bind to the causative agent such that the copper binding site is no longer able to bind copper or is able to bind it to a lesser extent. In this regard, the peptide may bind at or near the copper binding site and physically prevent the binding of copper. When the peptide binds at or near the copper binding site of Aβ it preferably binds at or near amino acids 5-14 of Aβ, more preferably amino acids 8-14 of Aβ and even more preferably at or near amino acid 13 of Aβ, which is a histidine residue.

Alternatively, the peptide may bind to the causative agent at a site removed from the copper binding site and disrupt the conformation (or 3-D structure) of the copper binding site to reduce or totally remove its ability to bind copper and/or its SOD activity. When the peptide disrupts the conformation of the copper binding site of Aβ it preferably binds and disrupts the conformation of amino acids 5-14 of Aβ, more preferably amino acids 8-14 and even more preferably amino acid 13 of Aβ.

In another form of the invention, the peptides are adapted to bind Aβ in a fashion that does not prevent or reduce copper binding but still has a therapeutic effect through at least reducing the SOD activity of the causative agent.

Functional variants also include peptides with modified or different amino acids sequences that still retain their ability to bind to the causative agent and inhibit its SOD activity and/or copper binding ability. These functional variants include peptides with deletions, insertions, inversions, repeats and/or type substitutions. Preferably, functional variants are at least 70%, 80% or 90% identical to SEQ ID NO:2, more preferably at least 95% identical to SEQ ID NO:2.

Functional variants also include peptides (i) in which one or more of the amino acid residues are substituted with a conserved or non-conserved amino acid residue such as synthetic, non-naturally occurring analogues and/or natural amino acid residues; or (ii) in which one or more of the amino acid residues includes a substituent group.

Particular conserved substitutions involve the substitution of a charged amino acid with an alternative charged amino acid or a negatively charged or neutral amino acid. Preferably, the changes are minor and do not have a negative impact on the ability of the peptide to bind to the causative agent and inhibit its copper binding ability and/or its SOD activity. Other conservative substitutions for the purposes of the present invention are exemplified hereunder. However, it will be appreciated that skilled persons may also determine further conservative substitutions not specifically listed.

| | |
|---|---|
| Aromatic | (Phenylalanine, Tryptophan, Tyrosine, Histidine) |
| Hydrophobic | (Leucine, Isoleucine, Valine, norleucine) |
| Small | (Alanine, Serine, Threonine, Methionine, Glycine) |
| Acidic | (Aspartic acid, Glutamic acid) |
| Basic | (Arginine, Lysine, Histidine) |
| Polar | (Glutamine, Asparagine) |

Preferably, the amino acids required for binding are a contiguous sequence of between about 5 and 20 amino acids and more preferably between about 6 and 15 amino acids.

Representative examples of useful peptides include any of the naturally occurring or synthetic di-, tri-, tetra-, pentapeptides or longer peptides derived from any of the above described amino acid sequences. Representative examples of useful polypeptides include both naturally occurring and synthetic polypeptides derived from the above described amino acids and peptides.

Nucleotides

The present invention also provides polynucleotides encoding the peptides of the invention. It will be understood by a skilled person that due to the degeneracy of the amino acid code, numerous different polynucleotides can encode the same peptide as a result of the degeneracy of the genetic code. In addition, it is to be understood that skilled persons may, using routine techniques, make nucleotide substitutions that do not affect the peptide sequence encoded by the polynucleotides of the invention to reflect the codon usage of any particular host organism in which the polypeptides of the invention are to be expressed.

Polynucleotides of the invention may comprise DNA or RNA. They may be single-stranded or double-stranded. They may also be polynucleotides that include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the present invention, it is to be understood that the polynucleotides described herein may be modified by any method available in the art. Such modifications may be carried out in order to enhance the in vivo activity or life span of polynucleotides of the invention.

Where the polynucleotide of the invention is double-stranded, both strands of the duplex, either individually or in combination, are encompassed by the present invention. Where the polynucleotide is single-stranded, it is to be understood that the complementary sequence of that polynucleotide is also included within the scope of the present invention.

Modified Peptides

The present peptide or analogues, such as those recited infra may be derivatized by the attachment of one or more chemical moieties to the peptide sequence. Chemical modification of biologically active peptides provides advantages under certain circumstances, such as increasing the stability and circulation time of the therapeutic peptides, decreasing immunogenicity and to enhance bioavailability and/or to enhance efficacy and/or specificity. See, U.S. Pat. No. 4,179, 337, Davis et al., issued Dec. 18, 1979. For a review, see Abuchowski et al., in Enzymes as Drugs. (J. S. Holcerberg and J. Roberts, eds. pp. 367 383 (1981)).

Chemical modification of one or more residues may be achieved by chemically derivatizing a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-imbenzylhistidine. Also included as chemical derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine.

In developing the invention the inventors have revealed that by stabilizing the peptides the half life of the peptide sequences can be substantially increased. Preferably the peptides are chemically derivatized to end protect the peptides (i.e. to protect the amino or carboxyl end of the sequence). By way of example, the peptides described in the Examples below were protected by acetylation of the amino terminus and amidation of the carboxyl terminus to improve stability.

Peptides of the invention may also be stabilised by derivatization using water soluble polymers. The polymer selected should be water soluble so that the peptide to which it is attached does not precipitate in an aqueous environment, such as a physiological environment. Preferably, for therapeutic use of the end-product preparation, the polymer will be pharmaceutically acceptable. One skilled in the art will be able to select the desired polymer based on such considerations as whether the polymer/peptide conjugate will be used therapeutically, and if so, the desired dosage, circulation time, resistance to proteolysis, and other considerations. The effectiveness of the derivatization may be ascertained by administering the derivative, in the desired form (i.e., by osmotic pump, or, more preferably, by injection or infusion, or, further formulated for oral, pulmonary or nasal delivery, for example), and observing biological effects as described herein.

The water soluble polymer may be selected from the group consisting of, for example, polyethylene glycol, copolymers of ethylene glycol/propylene glycol, carboxymethylcellulose, dextran, polyvinyl alcohol, polyvinyl pyrolidone, poly-1,3-dioxolane, poly-1,3,6-trioxane, ethylene/maleic anhydride copolymer, polyaminoacids (either homopolymers or random copolymers), and dextran or poly(n-vinyl pyrolidone)polyethylene glycol, propylene glycol homopolymers, polypropylene oxide/ethylene oxide co-polymers, polyoxyethylated polyols and polyvinyl alcohol. Polyethylene glycol propionaldenhyde may have advantages in manufacturing due to its stability in water. Also, succinate and styrene may also be used.

Desirably chemical moieties should be attached to the peptides at amino acid residues having a free amino group such as lysine residues and the N-terminal amino acid residue. Those having a free carboxyl group may include aspartic acid residues, glutamic acid residues, and the C-terminal amino acid residue.

Replacement of naturally occurring amino acids with a variety of uncoded or modified amino acids such as D-amino acids and N-methyl amino acids may also be used to modify peptides. For example, D amino acids can be substituted for L amino acids to increase in vivo stability of the peptides, while still retaining biological activity. Likewise, retro-inverso peptides, which contain NH—CO bonds instead of CO—NH peptide bonds, are much more resistant to proteolysis than L-peptides. Moreover, they have been shown to mimic natural L-peptides with respect to poly- and monoclonal antibodies. Therefore, peptides having at least one D amino acid on the amino terminal and/or carboxy terminal end of the molecule and which retain biological activity are considered part of the invention. In addition, retro-inverso peptides which contain one or more of the amino acid sequences of the invention and which retain biological activity are also considered part of the invention.

It may also be desirable to use derivatives of the peptides of the invention that are conformationally constrained. Conformational constraint refers to the stability and preferred conformation of the three-dimensional shape assumed by a peptide. Conformational constraints include local constraints, involving restricting the conformational mobility of a single residue in a peptide; regional constraints, involving restricting the conformational mobility of a group of residues, which residues may form some secondary structural unit; and global constraints, involving the entire peptide structure.

The active conformation of the peptide may be stabilized by a covalent modification, such as cyclization or by incorporation of gamma-lactam or other types of bridges. For example, side chains can be cyclized to the backbone so as to create a L-gamma-lactam moiety on each side of the interaction site. Cyclization also can be achieved, for example, by formation of cystine bridges, coupling of amino and carboxy terminal groups of respective terminal amino acids, or coupling of the amino group of a Lys residue or a related homolog with a carboxy group of Asp, Glu or a related homolog. Coupling of the alpha-amino group of a polypeptide with the epsilon-amino group of a lysine residue, using iodoacetic anhydride, can be also undertaken.

Another approach is to include a metal-ion complexing backbone in the peptide structure. Typically, the preferred metal-peptide backbone is based on the requisite number of particular coordinating groups required by the coordination sphere of a given complexing metal ion. In general, most of the metal ions that may prove useful have a coordination number of four to six. The nature of the coordinating groups in the peptide chain includes nitrogen atoms with amine, amide, imidazole, or guanidino functionalities; sulfur atoms of thiols or disulfides; and oxygen atoms of hydroxy, phenolic, carbonyl, or carboxyl functionalities. In addition, the peptide chain or individual amino acids can be chemically altered to include a coordinating group, such as for example oxime, hydrazino, sulfhydryl, phosphate, cyano, pyridino, piperidino, or morpholino. The peptide construct can be either linear or cyclic, however a linear construct is typically preferred. One example of a small linear peptide is Gly-Gly-Gly-Gly (SEQ ID NO:7) that has four nitrogens (an N4 complexation system) in the backbone that can complex to a metal ion with a coordination number of four.

Another approach is to use bifunctional crosslinkers, such as N-succinimidyl 3-(2 pyridyldithio) propionate, succinimidyl 6-[3-(2 pyridyldithio) propionamido]hexanoate, and sulfosuccinimidyl 6-[3-(2 pyridyldithio) propionamido]hexanoate.

The peptide may be prepared by attaching polyaminoacids or branch point amino acids. For example, the polyaminoacid may be an additional carrier peptide which, serves to increase the circulation half life of the sequence. For the present purpose of the present invention, such polyaminoacids should be those which have or do not create an antigenic response, or other adverse response.

A further technique for improving the properties of therapeutic peptides is to use non-peptide peptidomimetics. A wide variety of useful techniques may be used to elucidating the precise structure of a peptide. These techniques include amino acid sequencing, x-ray crystallography, mass spectroscopy, nuclear magnetic resonance spectroscopy, computer-assisted molecular modelling, peptide mapping, and combinations thereof. Structural analysis of a peptide generally provides a large body of data that comprise the amino acid sequence of the peptide as well as the three-dimensional positioning of its atomic components. From this information, non-peptide peptidomimetics may be designed that have the required chemical functionalities for therapeutic activity but are more stable, for example less susceptible to biological degradation.

One may mono-derivatize, or may provide for a di-, tri-, tetra- or some combination of derivatization, with the same or different chemical moieties.

Controlled release formulation may also be desirable. The drug could be incorporated into an inert matrix which permits release by either diffusion or leaching mechanisms. Slowly degenerating matrices may also be incorporated into the formulation. Another form of a controlled release of this therapeutic is by a system whereby the drug is enclosed in a semipermeable membrane which allows water to enter and push drug out through a single small opening due to osmotic effects. Some enteric coatings also have a delayed release effect.

The peptides described herein may be naturally occurring molecules. However, it will be appreciated that they may also be non-naturally occurring molecules that have been produced to mimic one or more characteristics of the naturally occurring molecules that are important for the screen. For example, the agent may be a construct comprising or mimicking the portion of the naturally occurring molecule that is required for SOD activity and/or copper binding. These agents can be constructed based on an analysis of the structure of the naturally occurring molecule that defines the parts of the molecule that are involved in copper binding and/or SOD activity. Once these parts are identified peptide mimetics with one or more characteristics of the natural molecule can be designed and used in the screen instead of the naturally occurring molecule.

Therapeutic Compositions

Peptides of the invention may be combined with various components to produce compositions of the invention. Preferably the compositions are combined with a pharmaceutically acceptable carrier or diluent to produce a pharmaceutical composition (which may be for human or animal use). Suitable carriers and diluents include isotonic saline solutions, for example phosphate-buffered saline.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. See, e.g., Remington's Pharmaceutical Sciences, 19th Ed. (1995, Mack Publishing Co., Easton, Pa.) which is herein incorporated by reference.

The preferred form of the pharmaceutical composition depends on the intended mode of administration and therapeutic application. Pharmaceutical compositions prepared according to the invention may be administered by any means that leads to the peptides of the invention coming in contact with a causative agent of a disease or disorder as herein described.

When treating AD patients a mode of administration will be through such routes of administration as intra cerebroventricular, parenteral, intramuscular, intravenous, subcutaneous, intraocular delivery, oral or transdermal administration by means of a syringe, optionally a pen-like syringe, or intra nasal, buccal and transdermal patch. Such administration will desirably may be by injection. Parenteral administration may also be used to introduce Pharmaceutical compositions into a patient. In an alternative form of the invention the pharmaceutical composition can be administered by means of an infusion pump.

The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the peptide. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy use with a syringe exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars such as mannitol or dextrose or sodium chloride.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Additionally, auxiliary substances, such as wetting or emulsifying agents, surfactants, pH buffering substances and the like can be present in compositions. Other components of pharmaceutical compositions are those of animal, vegetable, or synthetic origin oils, for example, peanut oil, soybean oil, and mineral oil. In general, glycols such as propylene glycol or polyethylene glycol are preferred liquid carriers, particularly for injectable solutions.

Additional formulations suitable for other modes of administration include oral, intranasal, and pulmonary formulations, suppositories, and transdermal applications The routes of administration described herein are intended only as a guide since a skilled practitioner will be able to determine readily the optimum route of administration and dosage for any particular patient.

Use of Peptides of the Invention

According to another aspect, the present invention provides a method for altering abnormal SOD activity and/or abnormal metal ion binding activity, said method comprising the step of: contacting a peptide as described herein with an agent that causes the abnormal SOD activity and/or abnormal metal ion binding, under conditions that promote contact of the peptide with the agent.

The invention also relates to a method for destabilizing multimeric forms of Aβ, comprising the step of: contacting a peptide sequence of the present invention with Aβ under conditions that facilitate binding of the peptide to the Aβ protein.

Diagnostic Methods

The current method in the diagnosis of AD is clinical by assessing symptomatic behaviour of the patient such as memory loss, language impairment, and dementia. However, a physician can only give a 'probable' diagnosis of AD for a living patient. The confirming of positive diagnosis of AD comes at autopsy with the detection of two types of brain lesions—Aβ plaques and neurofibrillary tangles. The development of methods for early-stage detection of AD will allow pre-symptomatic (e.g. sub-clinical) intervention with new disease modifying treatments targeting disease progression and before irreversible pathological changes occur. Such techniques will also prove useful in facilitating Phase II and III clinical trials and their potential will be evaluated as part of the clinical development plan for Alzhyme's AD therapeutics programmes.

In vivo detection and monitoring of AD includes administering a labelled Aβ peptide or active fragment thereof to a patient in an amount effective to bind with tissue evidencing the presence of, or susceptible to, AD. Like in vitro detecting methods, the presence of the labelled peptide or peptide fragment bound to tissue in the patient is detected by a known detecting technique that is appropriate to the tissue sample type, the particular peptide or fragment used, the labelling method used, and other such factors unique to the particular assay being performed.

Currently, one of the most sensitive methods for the early detection of AD and other neurodegenerative diseases is the use of functional imaging with positron emission tomography (PET). Other methods that might be used in the diagnostic methods of the invention include Single Photon Emission Computed Tomography (SPECT) or Magnetic Resonance Imaging (MRI).

In one particular aspect, the invention provides an AD monitoring system, which comprises: a peptide of the invention and a label useful for imaging by PET or SPECT or MRI or fluorescent imaging modalities.

Preferably, the label is a positron emitting radioisotope with a relatively short half-life, such as Iodine-125, Iodine-123, Fluorine-18 or Carbon-11. Such an isotope may be imaged by PET scanning. Magnetic resonance imaging may also be used, in which case the label would include a magnetically active particle. Alternative imaging modalities include the use of fluorescent reagents (Honigman et al, Mol. Therap. 4, 239 249, 2001) and Yang et al. Proc Natl Acad Sci 98, 2616 2621, 2001); the clinical use is still limited, because non-invasive detection is limited to pathological processes close to the surface, with a maximal depth of 10 cm in fluorescence-mediated tomography.

In another aspect the invention provides an in vivo detection method of AD in a patient, which method comprises the steps of: administering a labelled Aβ peptide or active fragment to the patient and detecting the presence of the labelled peptide or peptide fragment bound to the tissue in the patient by a known imaging technique. Imagining techniques that will have particular use with the present invention include PET, SPECT or MRI.

PET scanning using $^{11}$C-labelled Pittsburgh Compound-B has distinguished between people with AD from unaffected individuals but this compound visualizes Aβ plaques and thus focuses on the end-stage products of the disease. As SEQ ID NO: 2 or variants or analogues thereof bind to Aβ, they can be radio-labelled with Iodine-125, Iodine-123, Fluorine-18 or Carbon-11 and used as an imaging agent when coupled to something like PET to look at Aβ plaque load. Thus, the invention provides biomarkers that identify individuals with the early stages of Aβ pathology and then track disease course after treatment with candidate medications. In this instance the molecule of interest is SEQ ID NO: 2 or a variant or analogue thereof.

PET scanning will have particular value in the presented diagnostic methods. According to the PET methods certain isotopes emit positively charged particles of a mass close to zero (positrons) that otherwise have the wave properties of negatively charged electrons. If a positron and an electron collide, each particle undergoes conversion into a gamma ray of 511 keV energy; since both gamma rays are emitted into opposite directions at an angle of 180 degrees, it is feasible to scan such conversion events as coinciding gamma rays in paired detectors using e.g. lutetium oxyorthosilicate as scintillation detection material, while eliminating those gamma rays that do not coincide.

Due to the high cost in running dedicated PET systems, a less expensive imaging modality (single photon emission computed tomography, SPECT, also abbreviated SPET, for single photon emission tomography) has recently gained popularity whereby a gamma ray in the energy range of 30 to 300 keV energy is emitted and detected by a modified dual-head, or multiple head, gamma camera system. SPECT imaging can be performed with isotopes of longer half-life than those used in PET, such as $^{111}$In or $^{99}$mTc that are well-characterized in nuclear medicine and can be shipped from dedicated radiochemistry facilities. SPECT imaging has been found to be a safe and cost-effective method with advantages over other imaging methods in diagnosis and management of various disease states (Goldsmith and Kostakoglu, (2000) Radiol. Clinics North Am. 38, 511 to 524). Details of current SPECT instrumentation, especially novel useful SPECT/PET hybrid detection systems, are described in Fahey, (2001) Radiol. Clinics North Am 39, 919 to 929.

Methods of Treatment

In yet another aspect, the present invention provides a method for ameliorating or preventing a disease or disorder associated with abnormal SOD activity and/or abnormal metal ion binding in a patient, said method comprising the step of: administering to the patient an effective amount of a peptide as described herein under conditions that promote contact of the peptide with the agent causative of the abnormal SOD activity and/or abnormal metal ion binding.

A used herein the term "patient" generally includes mammals such as: humans; farm animals such as sheep, goats, pigs, cows, horses, llamas; companion animals such as dogs and cats; primates; birds, such as chickens, geese and ducks; fish; and reptiles.

The peptides of the present invention are adapted to bind to the causative agents of disease and remove their SOD activity and/or copper binding ability. Thus, the present invention also provides a method for ameliorating SOD activity or inhibiting the copper binding ability of a causative agent in a patient, the method comprising the step of: contacting the causative agent with a peptide as herein described such that the peptide binds with the causative agent in a fashion that at least reduces its SOD and/or copper binding activity.

Copper is involved in stabilizing multimeric forms of Aβ. Thus, the present invention also provides a method for destabilizing multimeric forms of Aβ, the method comprising the step of: contacting the multimeric Aβ with a peptide of the present invention such that the peptide binds to the multimeric Aβ in a fashion that destabilizes the multimeric Aβ. Preferably, this method is used to treat a patient afflicted with AD.

Further, the invention relates to methods for ameliorating or preventing the aggregation of Aβ in a patient, the method comprising the step of: contacting a therapeutically effective amount of peptide sequence of the present invention with Aβ under conditions that facilitate binding of the peptide to the Aβ protein. Preferably, this method is used to treat a patient afflicted with AD.

The present invention also concerns a method for treating or preventing a disease or disorder selected from the group comprising: type II diabetes, AD, Scrapie and Transmissible Spongiform Encephalopathies such as Creutzfeldt Jacob disease (CJD), variant CJD, Gerstmann Strausler Schinkler syndrome, Inclusion-Body Myositis and Bovine Spongiform Encephalopathy (BSE) comprising the step of: administering to the patient an effective amount of a peptide as described herein under conditions which promote contact of the peptide with the causative agent.

The present invention also concerns a method for treating or preventing an amyloid disease or disorder comprising the step of: administering to the patient an effective amount of a peptide as described herein under conditions which promote contact of the peptide with the causative agent of the disease or disorder.

Amyloid diseases or amyloidoses include a number of disease states having a wide variety of outward symptoms. These disorders have in common the presence of abnormal extracellular deposits of protein fibrils, known as "amyloid deposits" or "amyloid plaques". It is a general discovery of the present invention that amyloid diseases of the general forms discussed herein can be treated by administering peptide agents as herein described to destabilize the formation of these deposits.

Amyloid diseases include, without limitation, such disease states as (a) AA amyloidosis (caused by such ailments as chronic inflammatory disorders (eg rheumatoid arthritis, juvenile chronic arthritis, ankylosing spondylitis, psoriasis, psoriatic arthropathy, Reiter's syndrome, Adult Still's disease, Behcet's syndrome, and Crohn's disease), chronic local or systemic microbial infections (eg such as leprosy, tuberculosis, bronchiectasis, decubitus ulcers, chronic pyelonephritis, osteomyelitis, and Whipple's disease), and malignant neoplasms (eg Hodgkin's lymphoma, renal carcinoma, carcinomas of gut, lung and urogenital tract, basal cell carcinoma, and hairy cell leukaemia); (b) AL Amyloidoses which is generally associated with almost any dyscrasia of the B lymphocyte lineage, ranging from malignancy of plasma cells (multiple myeloma) to benign monoclonal gammopathy; (c) hereditary systemic amyloidoses; (d) Senile Systemic Amyloidosis; (e) Cerebral Amyloidosis; (f) Dialysis-related Amyloidosis (g) Hormone-derived Amyloidoses and (h) Miscellaneous Amyloidoses that are normally manifest as localized deposits of amyloid (such as idiopathic deposition include nodular AL amyloid, cutaneous amyloid, endocrine amyloid, and tumour-related amyloid).

The invention also extends to the treatment of Inclusion-Body Myositis (IBM). IBM is a progressive and debilitating muscle disease usually of persons over 50 years of age. It is of unknown cause and there is no successful treatment. Interestingly, however, there are remarkable pathologic similarities between IBM muscle and the AD brain. These include the abnormal accumulation, misfolding, and aggregation of Aβ; accumulation of APP, phosphorylated tau and other Alzheimer- and dementia-related proteins including presenilin, prion protein and a-synuclein; and the accumulation of cholesterol, apolipoprotein E and low-density lipoprotein receptors. It is now known that increased SOD-like activity and free radical toxicity are important in IBM pathogenesis. Given the role of oxidative stress in the progression of both AD and IBM, new treatments that target the oxidative injury process in AD are also likely to be effective in treating IBM.

Patients amenable to treatment include individuals at risk of disease but not showing symptoms, as well as patients presently showing symptoms of an amyloid disease or disorder. In the case of Alzheimer's disease, virtually anyone is at risk of suffering from Alzheimer's disease if he or she lives long enough. Therefore, the present methods can be administered prophylactically to the general population without the need for any assessment of the risk of the subject patient. The present methods are especially useful for individuals who do have a known genetic risk of Alzheimer's disease or any of the other hereditary amyloid diseases. Such individuals include those having relatives who have experienced this disease and those whose risk is determined by analysis of genetic or biochemical markers. A number of diagnostic tests are available for identifying individuals who have AD.

In asymptomatic patients, treatment can begin at any age (e.g., 10, 20, 30 years). Usually, however, it is not necessary to begin treatment until a patient reaches 40, 50, 60 or 70 years. Treatment typically entails multiple dosages of the peptides of the invention, preferably in a pharmaceutically acceptable form, over a period of time. If the response falls, a booster dosage is indicated.

In prophylactic applications, pharmaceutical compositions or medicaments are administered to a patient susceptible to, or otherwise at risk of, a particular amyloid disease or disorder in an amount sufficient to eliminate or reduce the risk or delay the outset of the disease.

In therapeutic applications, pharmaceutical compositions or medicaments are administered to a patient suspected of, or already suffering from such a disease in an amount sufficient to at least partially arrest, the symptoms of the disease and its complications. An amount adequate to accomplish this is defined as a therapeutically- or pharmaceutically-effective dose.

In both prophylactic and therapeutic regimes, agents are usually administered in several dosages until a sufficient response has been achieved. Typically, the response is monitored and repeated dosages are given if the response starts to wane.

Effective doses of the compositions of the present invention, for the treatment of the above described conditions vary depending upon many different factors, including means of administration, target site, physiological state of the patient, whether the patient is human or an animal, other medications administered, and whether treatment is prophylactic or therapeutic. Usually, the patient is a human, but in some diseases, such as prion protein-associated mad cow disease, the patient can be a nonhuman mammal, such as a bovine. Treatment dosages need to be titrated to optimize safety and efficacy.

Non-Limiting Illustration of the Invention

Further features of the present invention are more fully described in the following description. This description is included solely for the purposes of exemplifying the present invention. It should not be understood as a restriction on the broad description of the invention as set out above.

In Vitro Studies of Novel Peptides as Inhibitors of Human Aβ Function

Computer-based in silico modelling techniques were used to identify the core amino acids and the minimum sequence responsible for binding to the SOD-like activity site of Aβ. Those investigates lead to the identification of the following sequence, referred to as the 15merTNP:

(SEQ ID NO: 3)
Thr-Asn-Pro-Asn-Arg-Arg-Asn-Arg-Thr-Pro-Gln-Met-Leu-Lys-Arg

From this 15merTNP peptide, an peptide analogue, MP2, was developed, derived from the last 9 amino acids of the C-terminus of 15merTNP, and incorporating protection of the termini with N-acetyl (Ac) and C-amide ($NH_2$) groups. This peptide analogue MP2 was tested for its ability to inhibit Aβ's SOD-like activity and associated neurotoxicity in vitro, using the $H_2O_2$ DCF and MTS assays, respectively.

TABLE 1

Sequence of modelled peptide

| Modelled Peptide (MP)<br>(Peptide length)<br>[Comment] | Sequence |
| --- | --- |
| (9-mer)<br>[The termini are blocked by N-acetyl (Ac) and C-amide groups to help protect the peptide against proteolytic degradation]. | Ac-NRT*PQMLK*R-NH2<br>(SEQ ID NO: 2) |

Determination of Whether the Modelled Peptide Analogue MP2 Blocks Human Aβ1-42's SOD-Like Activity.

Aβ species were prepared and the assay run as described previously (i.e. Aβ1-42 at 200 nM and Copper and Dopamine concentrations remain unchanged). Peptide analogue MP2 (SEQ ID NO:2) was added to Aβ1-42+Cu solutions at ratios ranging from 0.005:1 to 10.0:1 (i.e. a ration of 0.005:1 would contain 1 nM of respective peptide). The peptide was dissolved in PBS pH7.5. The effect of MP2 on $H_2O_2$ production by human Aβ1-42 was determined in triplicate in three separate experiments (i.e. n=9) for doses ranging from 100 to 2000 nM (FIG. 1). These were compared against the level of $H_2O_2$ produced by human Aβ1-42 [test peptide analogue MP2+ positive control peptide 15merTNP; three experiments done in triplicate, thus n=36]. All data are presented as means±SEM.

For all assays run, the 15merTNP peptide (SEQ ID NO: 3), was included as a positive control for the assay and for comparing its activity with that of the modelled peptide analogue MP2. The effect of 15merTNP (200 nM) on $H_2O_2$ production by human Aβ1-42, was determined in triplicate in each of the 12 DCF assays (i.e. n=36) performed in this study. The 15merTNP peptide significantly reduced human Aβ1-42's $H_2O_2$ production by around 30% at 200 nM peptide (One way ANOVA; $F_{(1,70)}$=120.05, *P<0.001) as shown in FIG. 1 (i.e. TNP 200).

The addition of peptide analogue MP2 was shown to significantly alter $H_2O_2$ production by human Aβ1-42 (One way ANOVA; $F_{(6,110)}=64.31$, P<0.001). After post-hoc analysis, using Bonferroni correction, a significant reduction in $H_2O_2$ levels produced by human Aβ1-42 was observed at 100, and 200 nM of peptide MP2 (P<0.001). The maximum inhibition of human Aβ1-42's $H_2O_2$ production by peptide analogue MP2 was around 30% at 100 nM peptide, which is similar to 15merTNP at a similar concentration. However, peptide analogue MP2 also significantly increased $H_2O_2$ levels produced by human Aβ1-42 at doses≧1000 nM (P<0.001).

The DCF Fluorescence assay was also used to assess the efficacy of peptide analogue MP2 on reducing levels of $H_2O_2$ produced by human Aβ1-42. Results from these studies showed that only peptide analogue MP2 significantly reduced human Aβ1-42's $H_2O_2$ production, by as much as 30% at 100 nM peptide (One way ANOVA; $F_{(6,110)}=64.31$, P<0.001). The activity of peptide analogue MP2 is similar to that obtained for 15merTNP.

Assessment of the Ability of Peptide Analogue MP2 to Reduce Cell Death Induced by Human Aβ1-42

Figure 2:
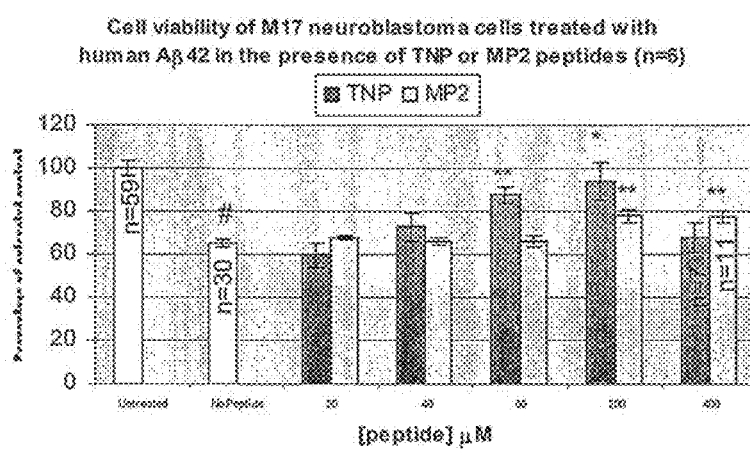
FIG. 2 illustrates the effect of SEQ ID NO: 2 on cell death associated with human Aβ1-42. Untreated vs No Peptide: ANOVA; $F_{(1,87)}=59.006$, # $P<0.001$; SEQ ID NO: 2: ANOVA; $F_{(5,60)}=6.32$, $P<0.001$; Post-Hoc (Bonferroni) **$P<0.05$, vs No Peptide.

M17 Neuroblastoma cells were seeded in a 48 well plate at a density of 50,000 cells per well. The plate was incubated for 24 hours at 37° C. in media (OPTI-MEM) containing 10% FCS. The next day the cells were treated with human Aβ1-42 (40 μM) in the presence or absence of the peptides 15merTNP or peptide analogue MP2 (FIG. 2). The peptides were provided at concentrations ranging from 20-400 μM prepared in Neuro basal media containing B27 supplement without antioxidants. Following incubation (4 days at 37° C.), cell viability was assessed using the CellTiter 96® AQueous One Solution cell proliferation assay (MTS; Promega, Wis., USA) as per manufactures instructions. Briefly, 200 μl of MTS reagent (1/10 dilution) was added directly to the culture wells and the plate incubated for 3 hours at 37° C. Following incubation, 150 μl of the solution was transferred to a 96 well plate and the absorbance is determined spectrophotometrically at 490 nm.

Similar to the MTT assay, the MTS assay is a colorimetric method for determining the number of viable cells in proliferation or cytotoxicity assays. The principle of the MTS assay is the same as the MTT assay, except for the tetrazolium compound that is bio-reduced by the mitochondria of the cells, forming a coloured formazan product that is soluble (rather than insoluble for the MTT assay) in tissue culture medium. This conversion is accomplished by NADPH or NADH produced by dehydrogenase enzymes in metabolically active cells: Berridge M V. And Tan A. S. (1993) Characterisation of the cellular reduction of 3-(4,5-dimethylthiazol-2-yl)-2,5-diphenyltetrazolium bromide (MTT): Subcellular localisation, substrate dependence and involvement of mitochondrial electron transport in MTT reduction. *Arch. Biochem. Biophys.* 303, 474-82.

Since the MTS formazan product is soluble in tissue culture medium, the MTS assay has the advantage over the MTT assay in that it requires fewer steps. The formazan product of MTT reduction is a crystalline precipitate that requires an additional step in the procedure to dissolve the crystals before recording absorbance readings (i.e. addition of DMSO). Thus, the MTS assay has a considerable advantage in that, after it is added to the cells, no further steps such as washing of cells, extraction of formazan crystals (using DMSO) or other manipulations are required. These considerations are important, particularly for high throughput screening of drug compounds.

The effect of human Aβ1-42 (40 μM) on cell viability was determined in triplicate in each of the 10 MTS assays (i.e. n=30) performed in this study. All data are presented as means±SEM. The results show that human Aβ1-42 (40 μM) significantly reduced cell viability by as much as 35% (One way ANOVA; $F_{(1,87)}=54.01$, P<0.001).

The effect of peptide analogue MP2 to protect against human Aβ42-induced toxicity was then determined using the MTS assay in triplicate in two separate experiments for all doses (i.e. n=6), unless otherwise specified. The effectiveness of MP2 was compared against the 15merTNP. In the MTS assay, the 15merTNP peptide significantly reduced cell death associated with human Aβ1-42 (40 μM) by 20% at 80 μM peptide [Post-Hoc (Bonferroni) **P<0.05] and 30% at 200 μM peptide [Post-Hoc (Bonferroni) *P<0.001] as shown in FIG. 2.

The addition of peptide analogue MP2 was shown to have no effect on cell death associated with human Aβ1-42 at concentrations≦80 μM (FIG. 2). At a concentration≧200 μM, peptide analogue MP2 significantly reduced cell death associated with human Aβ1-42 (P<0.05). The maximum reduction in cell toxicity associated with human Aβ1-42 by peptide analogue MP2 is around 15%.

From the cell viability experiments peptide analogue MP2 was effective at inhibiting human Aβ42-induced toxicity.

Based on the results from both the $H_2O_2$ (DCF) and MTS cell viability assays, peptide analogue MP2 significantly reduced human Aβ1-42's $H_2O_2$ production and cellular neurotoxicity.

Therapeutic Potential of the Peptide Analogue MP2

The following Examples evaluate the therapeutic potential of the 15merTNP (original 15-mer) and the peptide analogue MP2, which were delivered to the brain in a transgenic animal model of Alzheimer's disease (AD). Both 15merTNP and peptide analogue MP2 were selected as they were determined to be the most effective at modifying Aβ's SOD-like activity in vitro.

Additional research activities were divided into two parts: Stage 2A involved evaluating the in vitro stability of both 15merTNP and peptide analogue MP2 in biological media and then examining the brain uptake, distribution and pharmacokinetics of the peptides in vivo; and Stage 2B involved assessing the PS/APP mouse model for evidence of oxidative stress to determine its suitability for assessing the pharmacology of these peptides and finally to assess the efficacy of the most effective peptide (as determined in Stage 2A) in inhibiting Aβ-induced oxidative stress and neuro-inflammation in a transgenic animal model of AD.

Evaluation of the In Vitro Stability of Peptides of the Invention, In Vitro in Biological Media and their Pharmacokinetic Parameters In Vivo For the peptide stability assay in vitro, both 15merTNP and peptide analogue MP2 were incubated separately with fresh 10% rodent brain homogenate to model degradation in tissues. In order to create a physiological dose of peptide in the in vitro assay, both radioactive ($^3$H-labelled; hot) and non-radioactive (cold) peptides were combined in a set ratio. Cold peptide was added at a dose of 2.5 mmol per ml of 10% brain homogenate. Hot peptide was added at a dose of 250 μCi per ml 10% brain homogenate. Following the addition of hot and cold peptide; the homogenate was vortexed and incubated for different time points. The reaction was stopped by adding complete protease inhibitor cocktail and the samples analysed.

Figure 3:
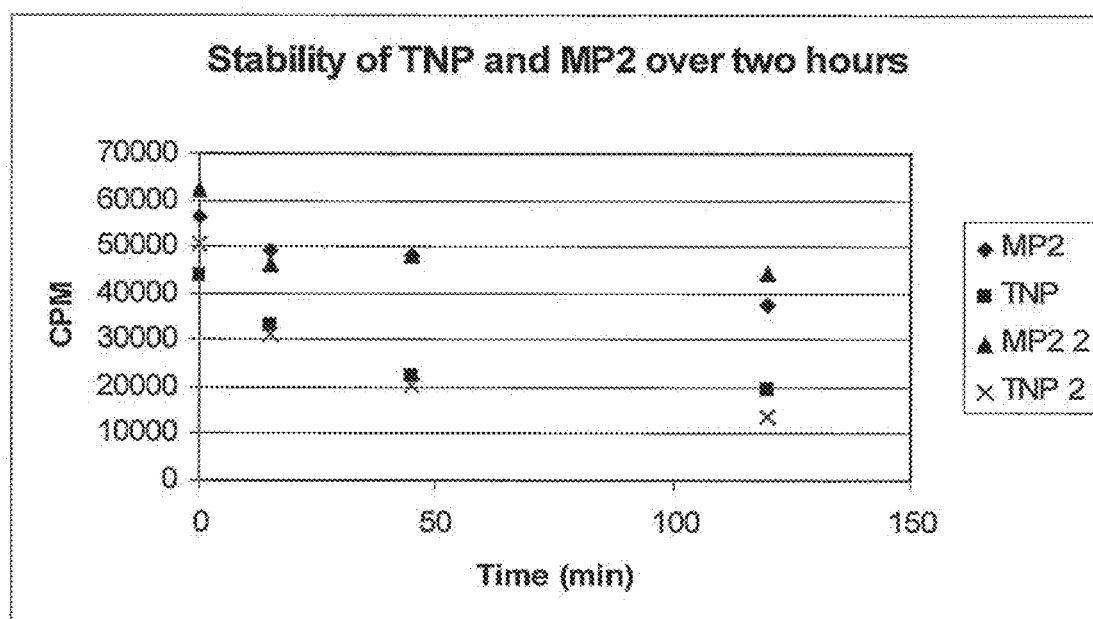
FIG. 3 illustrates the relative stability of TNP and SEQ ID NO: 2 over two hours run on a 16% Tricine gel from time 0-120 min with samples run in duplicate.

The results show that peptide analogue MP2 was significantly more stable than the 15merTNP in that it showed much slower degradation over a 24 hour time period, which is further demonstrated in FIG. 3.

TABLE 2

In vitro stability of selected peptides

| Peptide | Stability in rat brain homogenate |
|---|---|
| Peptide analogue MP2 | >24 hr |
| 15merTNP | <45 min |

The biological stability of the peptides was evaluated by incubating them (90 nmol) in fresh 10% rodent brain homogenate for different times at 37° C. The amount of intact peptide was estimated by running the supernatant of the homogenate on a 16% Tricine gel to separate peptide that had not had its amino acid sequence degraded. FIG. 3 illustrates the relative stability of 15merTNP and peptide analogue MP2 over two hours run on a 16% Tricine gel from time 0-120 min with samples run in duplicate. The values correspond to the in vitro half-life, which is defined as the time needed for 50% degradation of the peptide.

Results from these studies established that the pharmacological profile of peptides exhibited increased stability following chemical modification. Specifically, peptide analogue MP2 which was end protected by acetylation of the amino terminus and amidation of the carboxyl terminus, exhibited a half-life in physiological conditions of >24 hr compared to that for the unmodified/unprotected 15merTNP peptide which had a half life of <45 min.

In Vivo Blood-Brain Barrier (BBB) Permeability and Pharmacokinetic Studies

Another essential requirement of drug development is the ability of the peptide to cross the BBB and impact on targeted tissue. To measure the ability of 15merTNP and peptide analogue MP2 to cross the BBB, intracerebroventricular (i.c.v) delivery was assessed. The use of i.c.v injections on animal models allows for high doses to be delivered straight to the ventricular spaces where it can cross the parenchyma layer to the brain matter.

For i.c.v injections, control mice (129×1 strain) were anesthetized with intraperitoneal ketamine/xylazine at a dose of 10 ml/kg and then administered with 200 μg of either peptide (90 nmol). Both radioactive ($^3$H-labelled; hot) and non-radioactive (cold) was used to allow physiological doses of peptide to be delivered.

To determine whether the peptides had effectively penetrated into the brain parenchyma, a capillary depletion experiment was performed. After 25 min post injection the animal was sacrificed and the brain removed. This was homogenized and centrifuged for 10 min at 13000 rpm at 4° C. resulting in a supernatant containing predominately radioactivity from the cortex and a pellet with radioactivity from the capillaries and endothelium. A comparison of radioactivity in each sample was conducted to assess percentage of peptide movement into the cortex. The amount of radioactivity in the capillary pellet of mice that were perfused and not perfused with saline solution was compared to determine the percentage of peptide bound to the luminal surface of the capillaries and sequestered by brain endothelial cells.

A detailed necropsy was performed on each animal following perfusion to thoroughly assess peptide movement throughout peripheral organs, central nervous tissue and blood. A total of 16 tissues were removed from each mouse. All tubes were weighed prior to experimentation, and re-weighed prior to scintillation counting to ensure the exact mass of each tissue sample was known. Thus the concentration of labelled tritium could be measured per mass of sample and using this and the known ratio of non-labelled peptide present, the concentration of total peptide could be determined.

Figure 4:
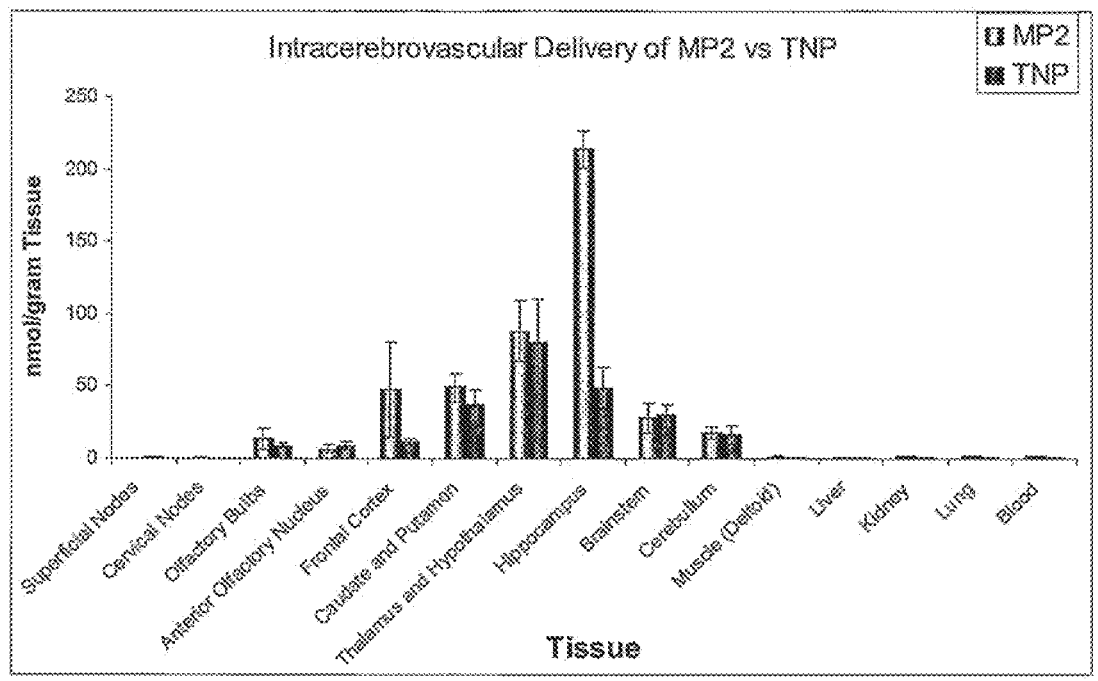
FIG. 4 illustrates the tissue concentrations of SEQ ID NO: 2 (nmol/g tissue) and TNP (nmol/g tissue) following intracerebrovascular delivery of 200 μg (90 nmol). Animals were sacrificed 25 min post peptide injection.
Figure 5:
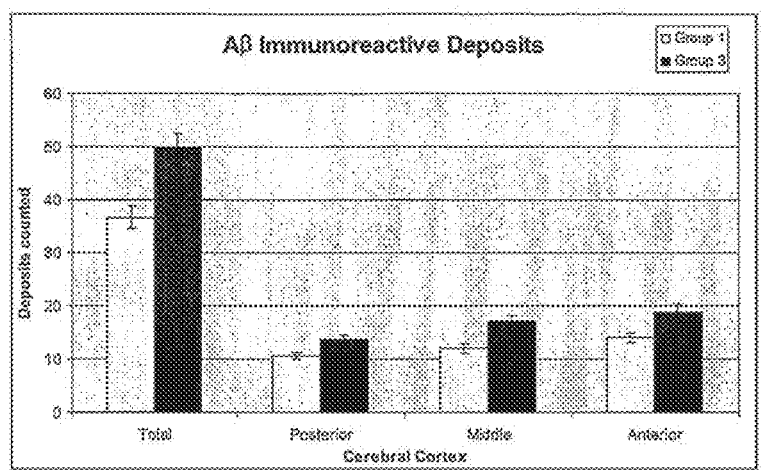
FIG. 5 illustrates the total number of Aβ immunoreactive deposits in the anterior, middle and posterior cerebral cortex of 6-month-old PS/APP transgenic mice treated with MP2 peptide (Group 1) or Vehicle (PBS; Group 3). * One way ANOVA $F_{(1,76)}$ $P<0.05$, # One way ANOVA $F_{(1,76)}$ $P<0.05$ after Ln transformation to normalize data.

I.c.v administration of 90 nmol [$^3$H]-MP2 and [$^3$H]-peptide analogue MP2 resulted in substantial delivery throughout the CNS and very little to the peripheral organs (FIG. 4). Peptide analogue MP2 showed higher delivery to the brain compared with 15merTNP (i.e. in frontal cortex, caudate, putamen, thalamus, hypothalaus and hippocampus). The highest concentration for both peptides was seen in the hippocampus (213.53 nmol/g peptide analogue MP2 and 80.51 nmol/g 15merTNP), followed by that thalamus and hypothalamus (87.87 nmol/g peptide analogue MP2 and 36.84 nmol/g 15merTNP), caudate and putamen (49.11 nmol/g peptide analogue MP2 and 36.84 nmol/g 15merTNP) and brainstem (27.94 nmol/g peptide analogue MP2 and 29.33 nmol/g 15merTNP). Peptide analogue MP2 showed higher concentrations in the blood than 15merTNP (1.67 nmol/g peptide analogue MP2 and 0.86 nmol/g 15merTNP). Low concentrations were seen in the deep (0.48 nmol/g peptide analogue MP2 and 0.39 nmol/g 15merTNP) and superficial cervical lymph nodes (0.26 nmol/g peptide analogue MP2 and 0.74 nmol/g 15merTNP).

The pharmacokinetic profile of peptide analogue MP2 over four time points, post i.c.v injection into the CNS was determined. From the results, the highest peptide concentration, post i.c.v. injection, was seen 25 minutes after delivery of the peptide into the ventricles. At the 5 min time point a relatively high concentration was seen in the immediate vicinity of the ventricles (hippocampus, thalamus and hypothalamus), predominately due to the slow rate at which peptide can be delivered via i.c.v. injection (total dose delivered over 20 min), allowing for early peptide movement to occur; this is most significantly demonstrated in the caudate, putamen, brainstem and cerebellum at the 5 min time point peptide analogue MP2 is seen to have high concentrations compared to other time points (25 min, 120 min and 180 min). Twenty five minutes post injection peptide analogue MP2 is seen to have the highest concentration in most tissues excluding lymph nodes, including peripheral organs, CNS and blood. Following 120 min over 80-90% of the peptide is seen to have diffused from the CNS compared to time point 25 min, this is seen to have increased to 90-99% at 180 minutes. This trend is further seen in peripheral organs with highest concentration at 25 min and progressively decreasing concentrations at 120 min (45-60% cleared) and 180 min (55-80% cleared). The only region of the body which showed increasing concentrations over time was the deep and superficial lymph nodes.

Therefore, both peptides have been shown to cross the blood brain barrier poorly. Furthermore this research has demonstrated that administration by i.c.v provides a mode of delivery of both peptide analogue MP2 and 15merTNP at concentrations similar to or above the physiological concentration of substances that are known to exert antioxidant effects in the human brain such as tocopherol (0.11-17.9 nmol/g), retinol (87.8-163.3 pmol/g) and carotenoids (1.8-23.0 pmol/g). Moreover peptide analogue MP2 is delivered in a dose dependant manner with higher doses providing higher efficacy of delivery to the CNS over peripheral tissues. This peptide is efficiently cleared/degraded from the CNS (99% of peptide removed within 3 hours) without any build-up in other organs.

Evaluation of the PS/APP Mouse Model for Evidence of Oxidative Damage

The presence of oxidative damage is critical to evaluating the efficacy of peptide analogue MP2 and 15merTNP peptide in vivo, since a proposed mechanism of action of these peptide is to inhibit Aβ's catalytic production of $H_2O_2$ by targeting the 'SOD-like site' of Aβ. It has previously been shown that oxidative damage to the CNS precedes Aβ plaque formation as indicated by increased levels of markers of oxidative stress (isoprostane levels) as seen in the PS/APP transgenic mouse AD model, which do not develop Aβ plaques until 3+ months.

Assessment of Peptide Analogue MP2 at Inhibiting Aβ-Induced Oxidative Stress and Neuro-Inflammation in a Transgenic Animal Model of CNS Aβ Deposition Peptide analogue MP2 [Ac-Asn-Arg-Thr-Pro-Gln-Met-Leu-Lys-Arg-NH2 (SEQ ID NO:2)] was delivered directly into the brain by i.c.v administration. For i.c.v infusion into the cerebrospinal fluid, a cannula is inserted into the right lateral ventricle of the brain (antero-posterior: −0.3 mm; medium-line: −1 mm; dorso-ventral: −2.2 mm) of 3-month and 6-month old PS/APP transgenic mice using a Kopf (Tujunga, Calif.) stereotaxic instrument (Permanne et al., 2002 "Reduction of amyloid load and cerebral damage in a transgenic mouse model of Alzheimer's disease by treatment with a β-sheet breaker peptide" *FASEB J.*).

The coordinates are measured from the Bregma and the surface of the skull according to the brain atlas of Franklin and Paxinos (The Mouse Brain in Stereotaxic Coordinates (1997) Academic Press, San Diego). The cannula is maintained on the skull with dental cement (Stoelting Company, Wood Dale, Ill.) and linked to a micro osmotic Alzet pump (model 2004; Alza Corporation, Palo Alto, Calif.) which is implanted under the back skin of the mice. The osmotic pumps are filled with either the peptide analogue, or vehicle (PBS). The treatments are infused over a period of 4 weeks at a rate of 0.25 μl/hour.

TABLE 4

Efficacy Study: Intraventricular Delivery of MP2 peptide or Vehicle in 6-month- and 3-month-old PS/APP Transgenic Mice

| Group No | Strain | Average Age | Treatment (Number of days = 28) | Number of Mice used for data analysis |
|---|---|---|---|---|
| 1 | PS/APP | 5.8 Months | MP2 Peptide (Dose: 60 nmoles/day) | 14 |
| 3 | PS/APP | 5.4 Months | Vehicle (PBS) | 13 |
| 4 | PS/APP | 2.6 Months | MP2 Peptide (Dose: 60 nmoles/day) | 13 |
| 6 | PS/APP | 2.6 Months | Vehicle (PBS) | 11 |

At the completion of treatment, animals are sacrificed and cardiac perfused with PBS. The brain is removed and the left cerebral hemisphere is used for histology and immunohistochemistry. The right hemisphere is used for measurement of Aβ.

For immunohistochemistry, tissue sections are cut and series of sections processed for peroxidase immunohistochemistry with antibodies specific for beta amyloid (1-42) and astrocytic activation (GFAP). Staining was performed using the DAKO Envision peroxidase labelled system (DAKO). Reactive astrocytes (forming a halo around Aβ deposits) were detected using antibody GFAP (1:500 dilution in DAKO antibody diluent; polyclonal, DAKO); Aβ detected using affinity purified WO2 antibody (1:10,000 dilution in Tris buffer (pH 7.6); raised against amino acid residues 5-8 of human Aβ, monoclonal). Brain sections on each slide were observed at 2.5× magnification using a Zeiss AXIO Imager.M1 microscope fitted with a Nikon DXM1200 colour digital camera. For both WO2 and GFAP stained sections, the number of Aβ immunoreactive deposits and GFAP immunoreactive Halo's present at 10× magnification (Objective EC Plan-Neofluar) were projected onto a screen and counted in three separate regions of the cerebral cortex, the posterior, middle and anterior.

For the measurement of human Aβ levels, brain extracts are prepared as described previously (Petanceska et al., 2000 "Ovariectomy and 17beta-estradiol modulate the levels of Alzheimer's amyloid beta peptides in brain" *Neurology*. 2000 Jun. 27; 54(12):2212-7) and a sensitive double-antibody sandwich ELISA assay employed as described previously (Mehta et al., 2000 "Plasma and cerebrospinal fluid levels of amyloid beta proteins 1-40 and 1-42 in Alzheimer's disease" *Arch Neurol*. 57(1):100-5).

Figure 6:
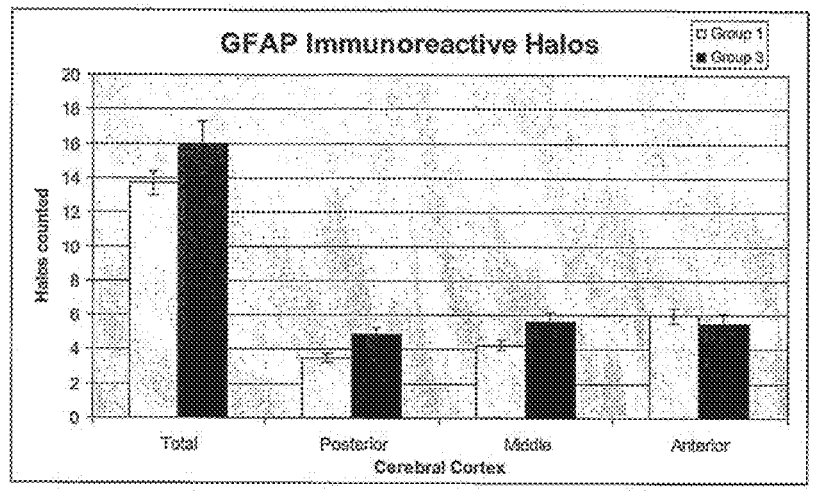
FIG. 6 illustrates the total number of GFAP immunoreactive halos in the anterior, middle and posterior cerebral cortex of 6-month-old PS/APP transgenic mice treated with peptide (Group 1) or Vehicle (PBS; Group 3). * One way ANOVA $F_{(1,75)}$ $P<0.05$, # One way ANOVA $F_{(1,73)}$ $P<0.05$. Both after Ln transformation to normalize data.

The results show that 6-month-old mice treated with 60 nmoles of MP2 peptide daily (Group 1) for 28 days by i.c.v infusion into the cerebrospinal fluid (via the right lateral ventricle of the brain), had a significantly reduced number of Aβ immunoreactive deposits compared to similar aged mice treated with Vehicle (PBS) only (Group 3) for the same period of time (FIG. 6). The treatment of MP2 resulted in 26.4% reduction in the estimated total number of Aβ immunoreactive deposits. This treatment effect was also observed upon stratifying count estimates by cortical region.

Figure 7:
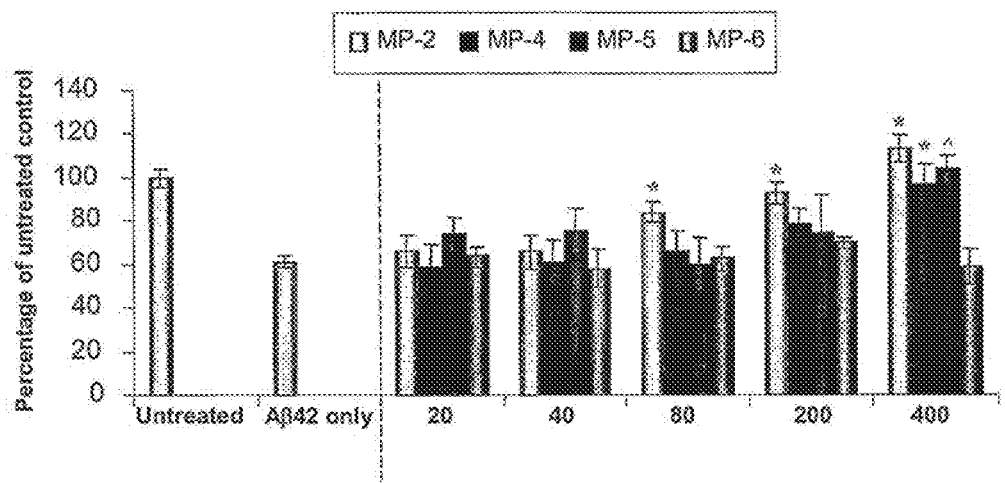
FIG. 7 illustrates the effect of various peptide analogues of the peptide analogue of SEQ ID NO:2 on cell viability associated with human Aβ1-42. Cells were treated with human Aβ42 peptide (20 μM) in the absence or presence of increasing doses of MP2, MP4, MP5 or MP6 (n=6, for each peptide). Cell viability was assessed by the MTS assay.

The treatment of 6-month-old PS/APP mice with MP2 peptide resulted in a reduction in the total number of GFAP immunoreactive halos, although significance was only reached in the middle and posterior cortical regions (FIG. 7).

Screening of Analogues of the Peptide Analogue MP2

A number of peptide analogs of MP2 (SEQ ID NO:2) were investigated.

```
MP-2                                  (SEQ ID NO: 2)
Ac-Asn-Arg-Thr-Pro-Gln-Met-Leu-Lys-Arg-NH2

MP-4                                  (SEQ ID NO: 4)
Ac-Arg-Thr-Pro-Gln-Met-Leu-Lys-NH2

MP-5                                  (SEQ ID NO: 5)
Ac-Thr-Arg-Thr-Pro-Gln-Met-Leu-Arg-Lys-NH2

MP-6                                  (SEQ ID NO: 6)
Ac-DArg-DLys-DLeu-DMet-DGln-DPro-DThr-DArg-
DAsn-NH2
```

Cells were treated with human Aβ42 peptide (20 μM) in the absence or presence of increasing doses of MP2, MP4, MP5 or MP6 (n=6, for each peptide). Cell viability was assessed by the MTS assay. Cell viability was significantly increased following treatment with human Aβ42 in the presence of MP2 (80-400 μM) or in the presence of 400 μM MP5 and MP6 (FIG. 7).

Figure 8A:
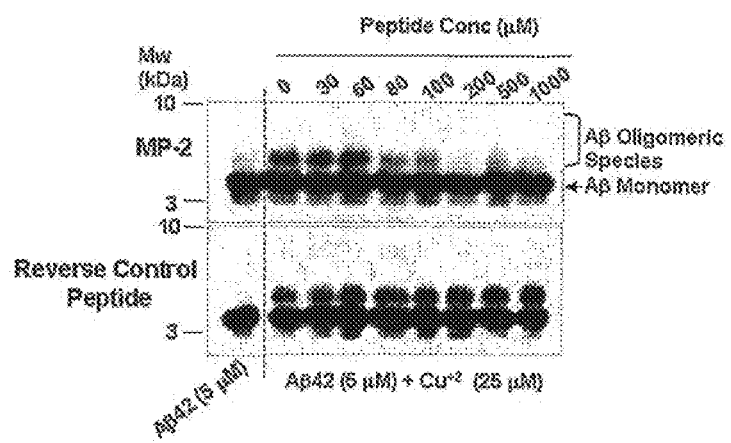
FIGS. 8A and 8B illustrate the effect of various peptide analogues of the peptide analogue of SEQ ID NO:2 on the generation of Aβ oligomers at various concentration.
Figure 8B:
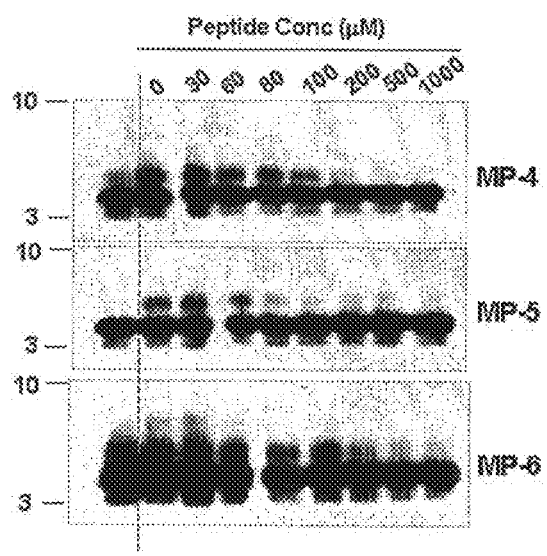

Incubation of Aβ with copper generates cross-linked oligomeric species (Atwood et al., 2000: Cell Mol Biol, 46: 777-783; Atwood et al., 2004: Biochemistry, 43: 560-568). In this experiment, Aβ (5 uM) is incubated with Cu+2 (25 μM) and 0-1000 μM of the modified peptides at 37 C for 24 hours. After the incubation period, 20 ng is loaded onto an SDS-PAGE gel and immunoblotted with WO2 antibody. Compared to the reverse peptide control, all the modified peptides inhibited the generation of Aβ oligomers at various concentration. MP-2, MP-4 and MP-5 were most potent at inhibiting Aβ oligomer formation (FIGS. 8A and 8B—representative of one experiment performed in duplicate).

Modifications of the above-described methods will be apparent to those skilled in the art. The above embodiments of the invention are merely exemplary and should not be construed to be in any way limiting.

The claims defining the invention are as follows:

1. A peptide capable of binding Aβ and disrupting its superoxide dismutase (SOD) activity and/or metal ion binding, wherein the peptide is selected from the group consisting of:
   (i) a peptide consisting of the amino acid sequence: Asn-Arg-Thr-Pro-Gln-Met-Leu-Lys-Arg (SEQ ID NO:2);
   (ii) a truncated form of the peptide (i) of at least 7 contiguous amino acids of SEQ ID NO:2;
   (iii) a peptide of 5, 6, 7, 8, or 9 amino acids, wherein the peptide sequence is at least 70% identical to SEQ ID NO:2;
   (iv) a peptide of 5, 6, 7, 8, or 9 amino acids, wherein the peptide sequence is at least 80% identical to SEQ ID NO:2; and
   (v) a peptide of 5, 6, 7, 8, or 9 amino acids, wherein the peptide sequence is at least 90% identical to SEQ ID NO:2.

2. A peptide according to claim 1 further comprising a water soluble polymer.

3. A peptide according to claim 1 comprising at least one amino acid.

4. A peptide according to claim 1 further comprising end protection at one or both its carboxy and amino ends.

5. A peptide according to claim 4 where the carboxy end is protected by amidation and the amino end is protected by acetylation.

6. A pharmaceutical composition comprising a peptide according to claims 1, 2, 3, 4 or 5.

7. A composition comprising a peptide according to any one of claims 1, 2, 3, 4 or 5 and a label useful for imaging by PET or SPECT or MRI or fluorescent imaging modalities.

* * * * *

UNITED STATES PATENT AND TRADEMARK OFFICE
CERTIFICATE OF CORRECTION

| | | |
|---|---|---|
| PATENT NO. | : 8,492,341 B2 | Page 1 of 1 |
| APPLICATION NO. | : 12/514738 | |
| DATED | : July 23, 2013 | |
| INVENTOR(S) | : Ralph Martins et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 423 days.

Signed and Sealed this
Tenth Day of February, 2015

Michelle K. Lee
*Deputy Director of the United States Patent and Trademark Office*